United States Patent
Kaneko et al.

(10) Patent No.: US 11,564,652 B2
(45) Date of Patent: Jan. 31, 2023

(54) STORAGE MEDIUM, DYNAMIC ANALYSIS APPARATUS, AND DYNAMIC ANALYSIS SYSTEM

(71) Applicant: Konica Minolta, Inc., Tokyo (JP)

(72) Inventors: Shikou Kaneko, Niiza (JP); Sumiya Nagatsuka, Hino (JP)

(73) Assignee: KONICA MINOLTA, INC., Tokyo (JP)

( * ) Notice: Subject to any disclaimer, the term of this patent is extended or adjusted under 35 U.S.C. 154(b) by 318 days.

(21) Appl. No.: 17/036,823

(22) Filed: Sep. 29, 2020

(65) Prior Publication Data

US 2021/0100519 A1    Apr. 8, 2021

(30) Foreign Application Priority Data

Oct. 4, 2019 (JP) .............................. JP2019-183406
Mar. 23, 2020 (JP) .............................. JP2020-050419

(51) Int. Cl.

| | | |
|---|---|---|
| *A61B 6/00* | (2006.01) | |
| *G06T 7/00* | (2017.01) | |
| *G16H 50/20* | (2018.01) | |
| *G16H 40/63* | (2018.01) | |
| *G16H 30/40* | (2018.01) | |
| *G16H 50/50* | (2018.01) | |
| *G16H 40/40* | (2018.01) | |
| *G16H 30/20* | (2018.01) | |

(52) U.S. Cl.
CPC ............ *A61B 6/5217* (2013.01); *A61B 6/463* (2013.01); *A61B 6/486* (2013.01); *A61B 6/487* (2013.01); *A61B 6/505* (2013.01); *A61B 6/5223* (2013.01); *A61B 6/5294* (2013.01); *G06T 7/0012* (2013.01); *G16H 30/20* (2018.01); *G16H 30/40* (2018.01); *G16H 40/40* (2018.01); *G16H 40/63* (2018.01); *G16H 50/20* (2018.01); *G16H 50/50* (2018.01); *A61B 6/468* (2013.01); *G06T 2207/10116* (2013.01); *G06T 2207/30008* (2013.01)

(58) Field of Classification Search
CPC ......... A61B 6/463; A61B 6/468; A61B 6/486; A61B 6/487; A61B 6/505; A61B 6/5217; A61B 6/5223; A61B 6/5294; G06T 7/0012; G06T 2207/10116; G06T 2207/30008; G16H 30/20; G16H 30/40; G16H 40/40; G16H 40/63; G16H 50/20; G16H 50/50
See application file for complete search history.

(56) References Cited

U.S. PATENT DOCUMENTS 7,230,262 B2 *   6/2007   Sendai .................. G03B 42/08
                                                     250/583

FOREIGN PATENT DOCUMENTS

| JP | H04-502387 A | 4/1992 |
|---|---|---|
| JP | 2009254472 A | 11/2009 |
| JP | 5397873 B2 | 1/2014 |

* cited by examiner

*Primary Examiner* — Mark R Gaworecki
(74) *Attorney, Agent, or Firm* — Lucas & Mercanti, LLP

(57) ABSTRACT

A non-transitory computer-readable storage medium storing a program causes a computer to perform an analysis process based on a radiation moving image in which a dynamic state of a specific site of a subject is captured. The program includes the analysis process in which, an analysis is performed based on the radiation moving image wherein when a plane in which the specific site is movable is to be a movable plane, the radiation moving image is obtained by irradiating radiation on the specific site in a state in which the radiation is orthogonal to the movable plane.

13 Claims, 18 Drawing Sheets

STORAGE MEDIUM, DYNAMIC ANALYSIS APPARATUS, AND DYNAMIC ANALYSIS SYSTEM

CROSS-REFERENCE TO RELATED APPLICATIONS

The entire disclosure of Japanese Patent Application No 2019-183406 filed on Oct. 4, 2019 and Japanese Patent Application No 2020-050419 filed on Mar. 23, 2020 is incorporated herein by reference in its entirety.

BACKGROUND

Technological Field

The present invention relates to a storage medium, a dynamic analysis apparatus, and a dynamic analysis system.

Description of the Related Art

When radiation imaging is performed, conventionally, the radiation is irradiated on a specific site as an imaging target so that the radiation is orthogonal to the surface of the specific site.

For example, JP 2009-254472 describes an X-ray imaging method in which an X-ray source, an X-ray imager, a rotation center of the above, and a subject are positioned to be in the following relation viewed in the irradiating direction of the X-ray beam, X-ray source, subject, rotation center, and X-ray imager. The subject image can move on the X-ray imager in a direction opposite to the direction in which the X-ray beam scans the subject and the direction in which the projected image moves on the X-ray image.

Conventionally, an X-ray source and an X-ray detector are provided, and the inside of the subject is seen through while irradiating a low dose of the X-ray on the subject (here, it is confirmed whether the catheter is reliably inserted in the blood vein). When the subject is in a predetermined state, a still image is imaged using an X-ray with a high dose (for example, a picture showing evidence that the catheter is reliably inserted).

SUMMARY

The radiation imaging is utilized to discover an abnormality in a joint, etc.

For example, the patella in the knee joint is known to move in a right and left direction with bending and stretching in the knee joint. However, if there is something abnormal in the knee joint, the movement of the patella may change non-continuously (for example, the movement may momentarily become fast) from somewhere during the movement.

If the non-continuous change in the movement can be kept as an image, it is possible to perform a more effective diagnosis to cure the abnormality in the knee joint.

However, according to the X-ray imaging method described in JP 2009-254472, the subject is fixed, and the X-ray source and the X-ray imager are moved. Therefore, if imaging is performed using such method, the specific site does not move and the non-continuous change in the movement cannot be captured in the image.

It is also possible to image a still image of the specific site while moving the state (bent angle) little by little and performing diagnosis based on the above. However, the above-described non-continuous change in the movement may not occur by such way of moving, and even if the change occurs, it may not be possible to image the moment.

When the subject is seen through, such non-continuous change in the movement may be discovered, but it is not possible to determine when such change in the movement occurs, and even if the change occurs, it happens for only one moment. Therefore, it is not easy for a doctor to perform diagnosis based on information obtained momentarily when the subject is seen through.

An object of the present invention is to easily perform diagnosis for a specific site in which there is a non-continuous change in the movement.

To achieve at least one of the abovementioned objects, according to an aspect of the present invention, a non-transitory computer-readable storage medium reflecting one aspect of the present invention, the non-transitory computer-readable storage medium storing a program causing a computer to perform an analysis process based on a radiation moving image in which a dynamic state of a specific site of a subject is captured, the program including: the analysis process in which, an analysis is performed based on the radiation moving image wherein when a plane in which the specific site is movable is to be a movable plane, the radiation moving image is obtained by irradiating radiation on the specific site in a state in which the radiation is orthogonal to the movable plane.

According to another aspect of the present invention, a dynamic analysis apparatus includes: a hardware processor which is configured to perform an analysis based on a radiation moving image in which a dynamic state of a specific site of a subject is captured, wherein, when a plane in which the specific site is movable is to be a movable plane in the radiation moving image, the hardware processor performs the analysis based on the radiation moving image obtained by irradiating radiation to the specific site to be orthogonal to the movable plane.

According to another aspect of the present invention, a dynamic analysis system includes: a moving image generator which generates a radiation moving image in which a dynamic state of a specific site of a subject is captured; and a hardware processor which is configured to perform an analysis based on the radiation moving image, wherein, when a plane in which the specific site is movable is to be a movable plane in the radiation moving image, the hardware processor performs the analysis based on the radiation moving image obtained by irradiating radiation to the specific site to be orthogonal to the movable plane.

BRIEF DESCRIPTION OF THE DRAWINGS

The advantages and features provided by one or more embodiments of the invention will become more fully understood from the detailed description given hereinafter and the appended drawings which are given by way of illustration only, and thus are not intended as a definition of the limits of the present invention, and wherein.

DETAILED DESCRIPTION OF EMBODIMENTS

An embodiment of the present invention is described with reference to the drawings. However, the scope of the present invention is not limited by the embodiments and diagrams shown below.

1. Dynamic Analysis System

Figure 1:
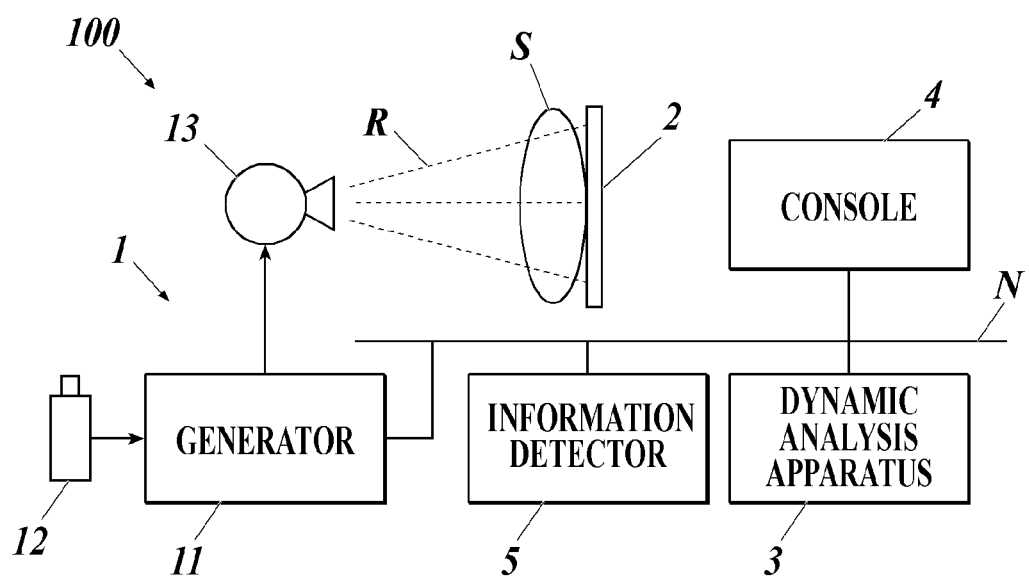
FIG. 1 is a block diagram showing a dynamic analysis system according to an embodiment of the present invention.
Figure 2A:
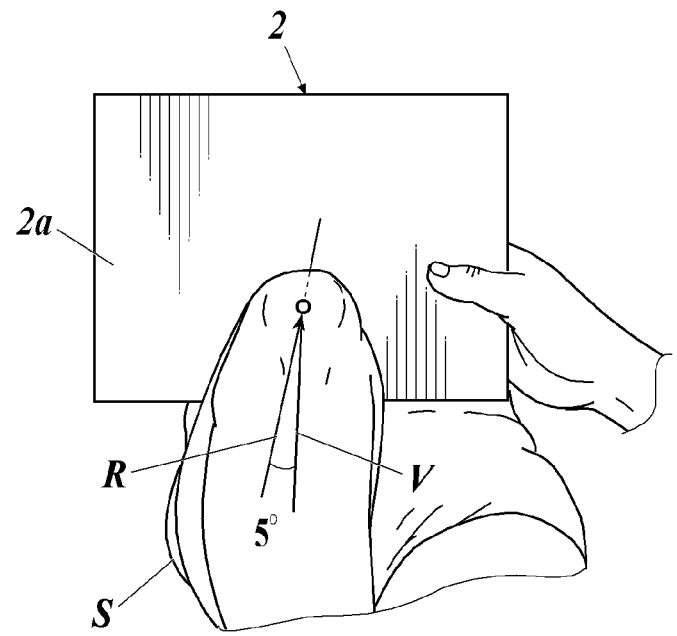
FIG. 2A is a diagram showing an example of how to image a specific site.
Figure 2B:
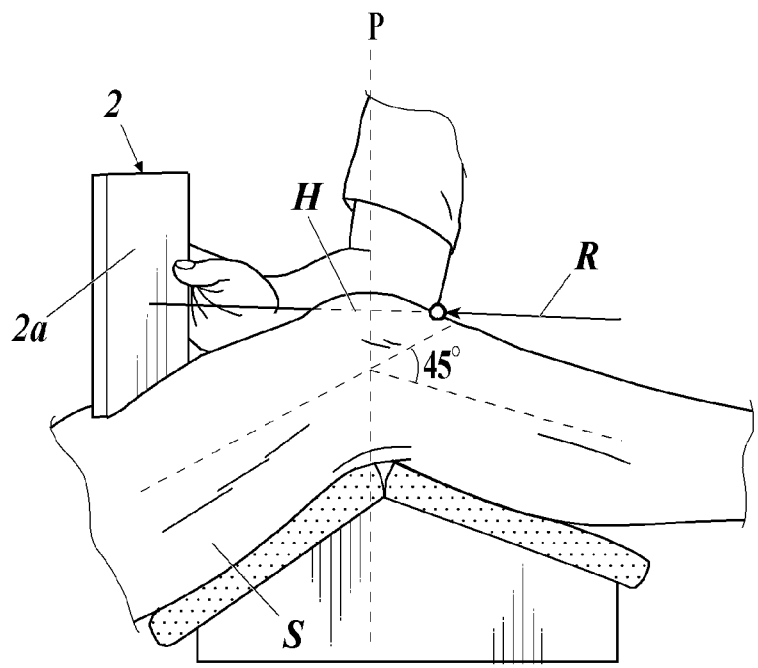
FIG. 2B is a diagram showing an example of how to image a specific site.

First, a summary of the configuration of a dynamic analysis system (hereinafter referred to as system 100) according to the present embodiment is described. FIG. 1 is a block diagram showing a system 100, FIG. 2A and FIG. 2B are diagrams showing an example of how a specific site is imaged, and FIG. 3A to FIG. 6 are diagrams showing an example of a movement in the specific site.

As shown in FIG. 1, the system 100 includes a radiation generating apparatus 1, a radiation detector 2, and a dynamic analysis apparatus 3.

The system 100 according to the present embodiment further includes a console 4 and an information detector 5.

The above apparatuses 1 to 5 are able to communicate with each other through a communication network N (LAN (Local Area Network), WAN (Wide Area Network), the internet, etc.).

The system 100 can communicate with a Hospital Information System (HIS), a Radiology Information System (RIS) or a Picture Archiving and Communication System (PACS) (illustration omitted for the above).

(Radiation Generating Apparatus)

The radiation generating apparatus 1 includes a generator 11, an irradiating instruction switch 12, and a radiation source 13.

The radiation generating apparatus 1 can be provided fixed in an imaging room or can be moved in a diagnosis car with the console 4.

Based on the irradiating instruction switch 12 being operated, the generator 11 applies voltage to the radiation source 13 (tube) according to imaging conditions (for example, condition regarding a subject S such as imaging site, imaging direction, physique, and conditions regarding irradiating of radiation R such as tubular voltage, tubular current, irradiating time, and electric current time product (mAs value)) set in advance.

When the voltage is applied from the generator 11, the radiation source 13 generates a dose of radiation R (for example, X-ray) according to the applied voltage.

The radiation source 13 is able to move in an X-axis direction, a Y-axis direction orthogonal to the X-axis, and a Z-axis direction orthogonal to the X-axis and the Y-axis. The radiation source 13 is able to rotate around a rotating axis parallel to the Y-axis and the Z-axis so as to be able to change a direction of an irradiating opening of the radiation.

By configuring the radiation generating apparatus 1 as described above, the radiation R can be generated in a state according to the imaging style (still image imaging, moving image imaging).

Moreover, as shown in FIG. 2A, the radiation generating apparatus 1 is able to irradiate radiation R to any site (knee, shoulder, elbow, wrist, etc.) of the subject S in any posture (standing, lying, sitting) so that an irradiating direction (extending direction of optical axis of radiation) forms any angle with relation to a horizontal surface H and a vertical line V.

That is, the radiation generating apparatus 1 functions as the radiation irradiator.

(Radiation Detector)

Although illustration is omitted, the radiation detector 2 includes the following. A sensor substrate in which pixels provided with radiation detecting elements which generate charge according to a dose of received radiation R and a switch element which accumulates and discharges charge are arranged two-dimensionally (matrix shape), a scanning circuit which switches on and off of the switch elements, a reading circuit which reads the amount of charge discharged from each element as a signal value, a controller which generates a radiation image from the plurality of signal values read by the reading circuit, and a communicator which transmits generated radiation image data and various signals outside and which receives various information and various signals.

The radiation detector 2 synchronizes with the timing in which the radiation R is irradiated from the radiation generating apparatus 1, and performs accumulating and discharge of the charge and the reading of the signal value. With this, the radiation image is generated according to the dose of the irradiated radiation.

Specifically, when the moving state of the specific site is imaged, the charge is accumulated and discharged and the reading of the signal value is repeated a plurality of times within a short time (for example, 15 times within one second). With this, the radiation moving image including a plurality of frames is generated.

That is, the radiation detector 2 functions as the moving image generator.

As shown in FIG. 2B, with relation to the radiation R irradiated in any direction, the radiation detector 2 according to the present embodiment is able to position a radiation entering surface 2a on a line extending in the irradiating direction of the radiation R with the specific site in between.

The radiation detector 2 is positioned alone in FIG. 2A and FIG. 2B, but alternatively, the radiation detector 2 can be supported by an imaging stage not shown.

(Dynamic Analysis Apparatus)

The dynamic analysis apparatus 3 includes a PC or a dedicated apparatus.

The dynamic analysis apparatus 3 analyzes the moving state of the specific site based on the radiation moving image in which the dynamic state of the specific site of the subject S is captured.

Details of the dynamic analysis apparatus 3 are described below.

(Console)

The console 4 includes a PC or a dedicated apparatus.

Based on imaging order information obtained from another system (HIS, RIS, etc.) or user operation, the console 4 sets various imaging conditions (tubular voltage, tubular current, irradiating time (mAs value) imaging site, imaging direction, etc.) in the imaging apparatus.

FIG. 1 shows a system 100 including the dynamic analysis apparatus 3 different from the console 4, but the console 4 can be formed as one with the dynamic analysis apparatus 3.

(Information Detector)

The information detector 5 detects external information occurring while the radiation detector 2 generates the radiation moving image (while performing moving image imaging).

The information detector 5 according to the present embodiment includes a microphone positioned near the subject S and pressing buttons which can be operated by the subject S.

Such "external information" is the voice emitted by the subject S when the subject S feels pain when bending and extending the joint during imaging, or the operation signal output when the subject S presses the pressing button when the subject S feels pain.

When the information detector 5 detects external information, the information detector 5 transmits the information detecting signal showing that the external information is detected to the dynamic analysis apparatus 3.

The information detector 5 functions as the detector according to such operation.

The information detector 5 may transmit the information detecting signal to other apparatuses which handle the radiation moving image data (for example, radiation detector 2, console 4, etc.).

(Summary of Operation of Dynamic Analysis System)

According to the system 100 configured as described above, the radiation source of the radiation generating apparatus 1 and the radiation detector 2 are positioned facing each other with a space in between, and the radiation R is irradiated from the radiation source 13 to the specific site in the subject S who is positioned between the above devices. With this, the radiation image of the subject S can be imaged.

When the subject is imaged in a still state, irradiating of the radiation R and the generating of the radiation image is performed only once for one imaging operation (pressing of the irradiating instruction switch), and when the moving state of the specific site is imaged, the irradiation of the pulsed radiation R and the generating of the frame is repeated a plurality of times in a short time for one imaging operation.

The system 100 transmits the moving image generated by the radiation detector 2 to the dynamic analysis apparatus 3, and the dynamic analysis apparatus 3 analyzes the dynamic state of the specific site captured in the moving image.

(Dynamic State of Analysis Target)

The system 100 is able to perform analysis for a dynamic state in any specific site.

However, the system 100 according to the present embodiment is suitable for analysis of the specific site moving along a specific movable plane P, that is, analysis based on the radiation moving image obtained by irradiating the radiation R so as to be orthogonal with the movable plane P with relation to the specific site.

Such specific site including the specific movable plane P includes joints or a spine.

The system 100 according to the present embodiment sets a patella $B_1$ of a knee joint as a specific site from among the above.

Figure 3A:
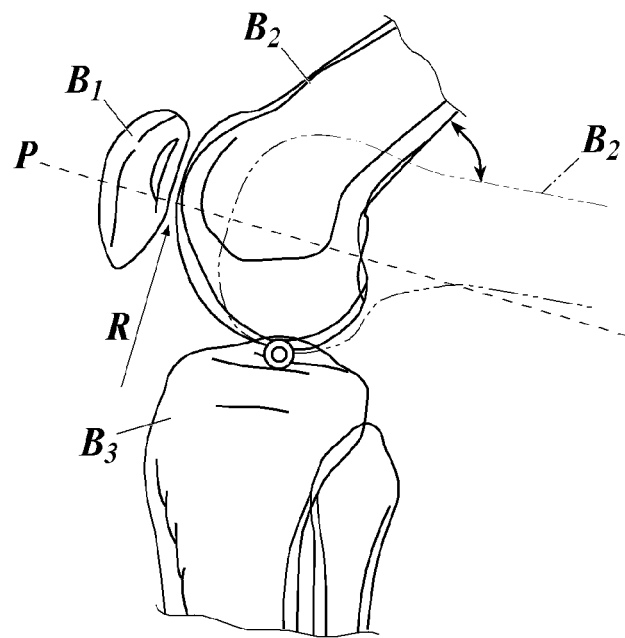
FIG. 3A is a diagram showing an example of a movement of a specific site.
Figure 3B:
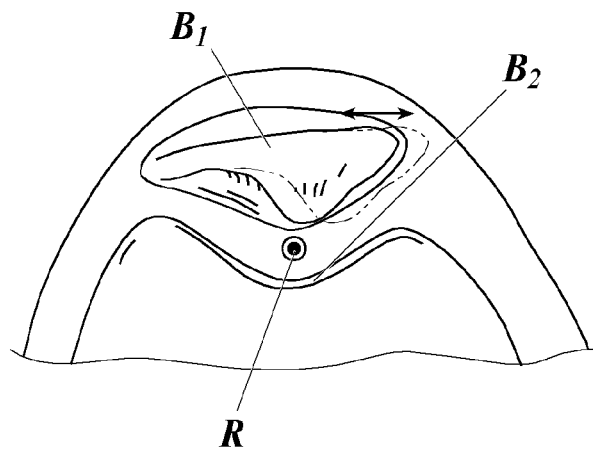
FIG. 3B is a diagram showing an example of a movement of a specific site.

As shown in FIG. 3A to FIG. 3B, together with the bending and extending of the knee, it is known that the patella $B_1$ moves in a direction orthogonal to each of an extending direction of a femur $B_2$ and an extending direction of a tibia $B_3$ (direction orthogonal to the sheet in FIG. 3A and the direction left to right in FIG. 3B).

When there is an abnormality in the knee joint, the movement of the patella changes non-continuously when moved along the movable plane P.

Such "non-continuous" change in the movement includes sudden movements such as the movement suddenly becoming fast, direction of the movement suddenly changing, or the like.

Therefore, as shown in FIG. 2B and FIG. 3A, if the radiation R is irradiated to the knee joint to be orthogonal with the movable plane P of the patella $B_1$ with the bending and extending of the knee (plane which passes the straight line extending in the moving direction of the patella $B_1$), and the imaging is performed, the non-continuous change in the movement of the patella B, can be captured in the radiation moving image.

Figure 4:
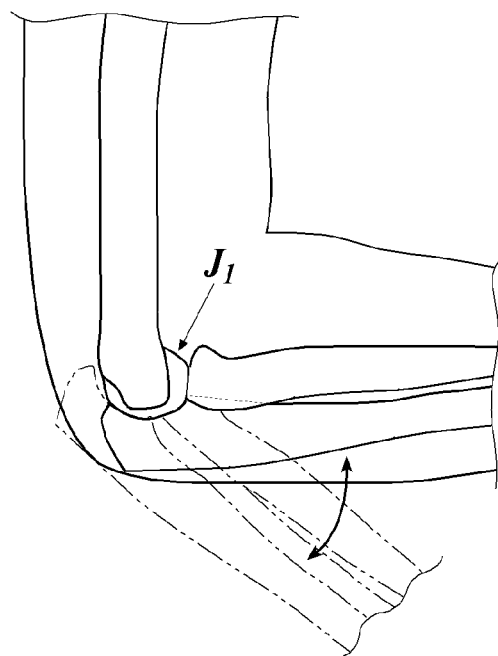
FIG. 4 is a diagram showing another example of the movement of the specific site.

The specific site can also be an elbow joint $J_1$ when bending and extending is performed as shown in FIG. 4.

In this case, the surface passing the elbow joint $J_1$, an axis of a humerus and an axis of a radius is to be the movable plane P (plane along the sheet of FIG. 4).

Figure 5A:
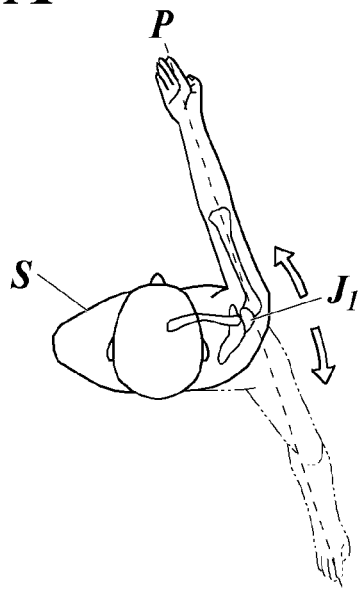
FIG. 5A is a diagram showing another example of the movement of the specific site.
Figure 5B:
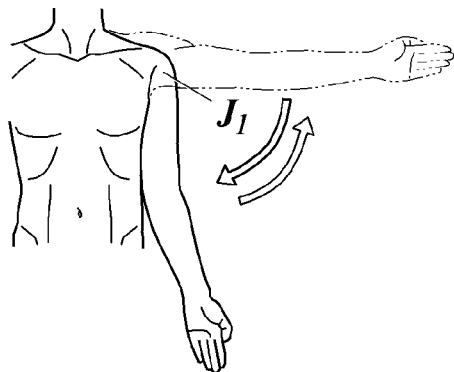
FIG. 5B is a diagram showing another example of the movement of the specific site.
Figure 5C:
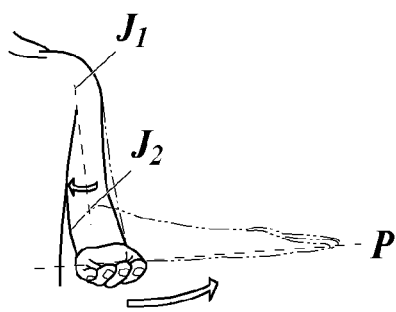
FIG. 5C is a diagram showing another example of the movement of the specific site.

The specific site can be a shoulder joint $J_2$ doing, for example, bending and extending as shown in FIG. 5A, adduction and abduction as shown in FIG. 5B, or internal rotation and external rotation as shown in FIG. 5C.

In this case, the plane which passes the shoulder joint $J_2$ and the axis of the humerus and the plane passing the elbow joint $J_1$ and the axis of the fore arm is to be the movable plane P.

Figure 6:
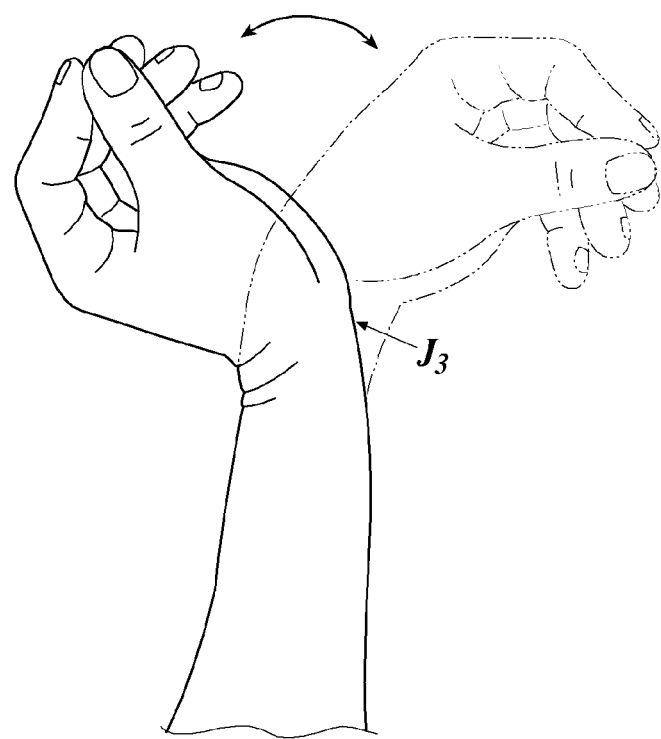
FIG. 6 is a diagram showing another example of the movement of the specific site.

Moreover, the specific site can be the hand joint $J_3$ when the bending and extending as shown in FIG. 6 is performed.

In this case, the plane which passes the hand joint $J_3$, the axis of the radius and the axis of the metacarpal bone is to be the movable plane P (plane along the sheet of FIG. 6).

2. Dynamic Analysis Apparatus

Next, the specific configuration of the dynamic analysis apparatus 3 included in the system 100 is described.

Figure 7:
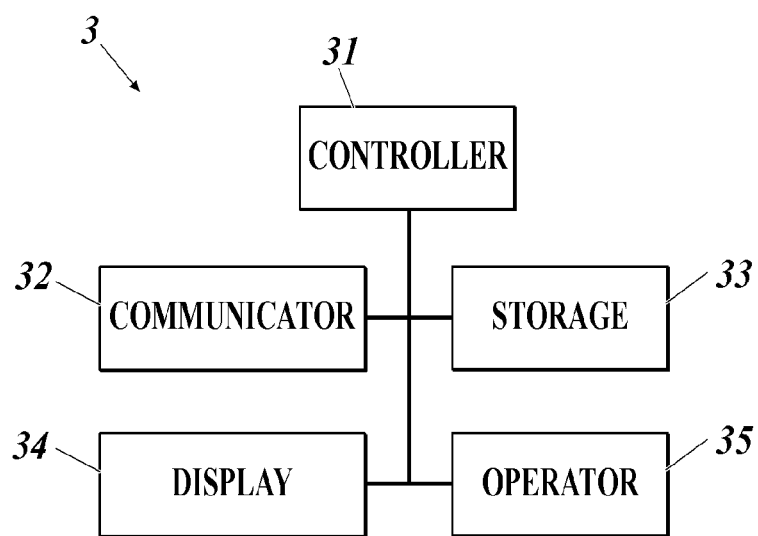
FIG. 7 is a block diagram showing a dynamic analysis apparatus included in a radiation imaging system as shown in FIG. 1.
Figure 8:
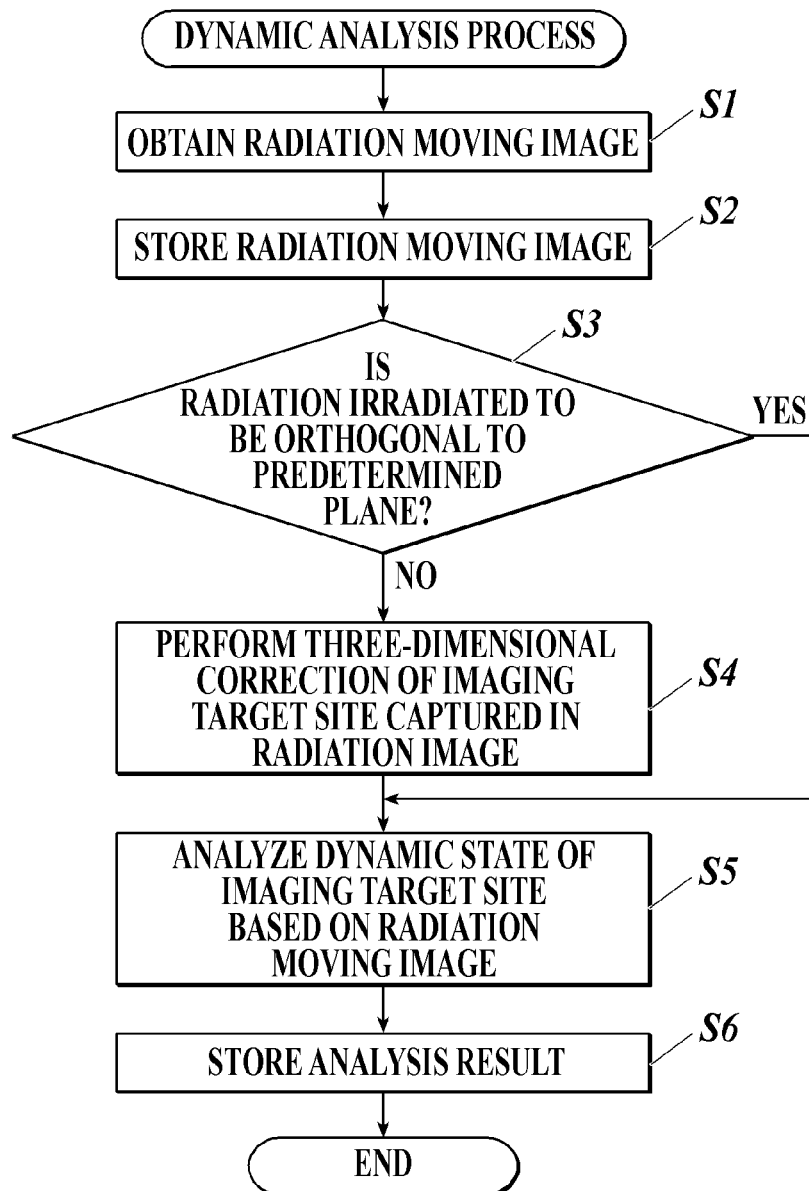
FIG. 8 is a diagram showing a flowchart showing a flow of a dynamic analysis process executed by the dynamic analysis apparatus as shown in FIG. 7.

FIG. 7 is a block diagram showing the dynamic analysis apparatus 3, and FIG. 8 is a flowchart showing the flow of the dynamic analysis process performed by the dynamic analysis apparatus 3.

[Configuration of Dynamic Analysis Apparatus]

As shown in FIG. 7, the dynamic analysis apparatus 3 includes a controller 31, a communicator 32, and a storage 33.

The dynamic analysis apparatus 3 according to the present embodiment further includes a display 34, and an operator 35.

The units 31 to 35 are electrically connected by a bus, etc.

The controller 31 includes a CPU (Central Processing Unit) and a RAM (Random Access Memory).

The CPU of the controller 31 (hardware processor) reads the various programs stored in the storage 33 and deploys the programs in the RAM. The CPU of the controller 31 executes various processes according to the deployed programs and centrally controls the operations in each unit of the dynamic analysis apparatus 3.

The communicator 32 includes a communicating module.

The communicator 32 is able to transmit and receive various signals and various data between other apparatuses (for example, the radiation detector 2, the console 4, etc.) connected through the communication network N.

The dynamic analysis apparatus 3 may include a reader which can read the contents stored in the storage medium instead of the communicator 32 and may take in various data using the storage medium.

The storage 33 includes a nonvolatile semiconductor memory and hard disk.

The storage 33 stores various programs executed by the controller 31 (including later-described dynamic analysis process) and the parameters necessary to execute the program.

The storage 33 can store the radiation image.

The display 34 includes a monitor which displays an image such as a LCD (Liquid Crystal Display) or CRT (Cathode Ray Tube).

Based on the control signal input from the controller 31, the display 34 displays various images.

The operator 35 according to the present embodiment includes a keyboard including a cursor key, numeric input keys, and various functions keys, a pointing device such as a mouse, and a touch panel layered on a surface of the display 34.

The operator 35 outputs a control signal according to the operation by the user to the controller 31.

At least one of the display 34 and the operator 35 can be used common with the console 4.

(Operation of Dynamic Analysis Apparatus)

The controller 31 according to the dynamic analysis apparatus 3 configured as described above includes the following functions.

Analysis Function

For example, based on a predetermined condition being satisfied, the controller 31 performs the dynamic analysis process as shown in FIG. 8.

Such "predetermined condition" includes, for example, turning the power on, connecting to the communication network N, performing a predetermined start operation on the operator 35, or the communicator 32 receiving the predetermined control signal from another apparatus.

In the dynamic analysis process, first, the controller 31 performs an obtaining process (step S1).

In such obtaining process, the controller 31 obtains the radiation moving image which is to be a target of analysis from another apparatus.

The controller 31 according to the present embodiment receives the data through the communicator 32 and obtains the radiation moving image.

The data is obtained by reading the data stored in the storage medium.

The controller 31 may start the dynamic analysis process when the radiation moving image is obtained. In this case, there is no need to perform the obtaining process in the dynamic analysis process.

After the radiation moving image is obtained, the controller 31 according to the present embodiment performs a storage process (step S2).

In the storage process, the controller 31 stores at least one of the plurality of frames included in the obtained radiation moving image in the storage 33.

That is, the storage 33 functions as a storage unit.

The controller 31 according to the present embodiment stores all of the frames.

The controller 31 may store the frame in the later-described second storage process without executing this storage process.

The controller 31 may transmit the radiation moving image to another apparatus (console 4, or a server not shown) including a storage and store the radiation moving image in the storage instead of storing the radiation moving image in the storage 33.

After storing the radiation moving image, the controller 31 according to the present embodiment performs a determining process before performing a later-described analysis process (step S3).

In the determining process, the controller 31 determines whether the radiation R is irradiated to the specific site $B_1$ so as to be orthogonal to the movable plane P when the specific site $B_1$ is imaged.

In the determining process, the controller 31 according to the present embodiment determines whether the radiation R is irradiated to be orthogonal to the movable plane P based on the setting state of the radiation generating apparatus 1.

In the determining process, the controller 31 does not have to determine that the state is orthogonal only when the angle between the optical axis of the radiation R and the movable plane P is 90°, and for example, the controller 31 may determine whether the angle is within the range of 90°±10°.

According to the determining process, when it is determined that the radiation R is not irradiated to the specific site $B_1$ to be orthogonal to the movable plane P (step S3: NO), the controller 31 according to the present embodiment performs the correction process (step S4).

In this correction process, the controller 31 rotates the specific site $B_1$ captured in the radiation moving image three-dimensionally so that the radiation R is irradiated to be orthogonal to the movable plane P.

Figure 9:
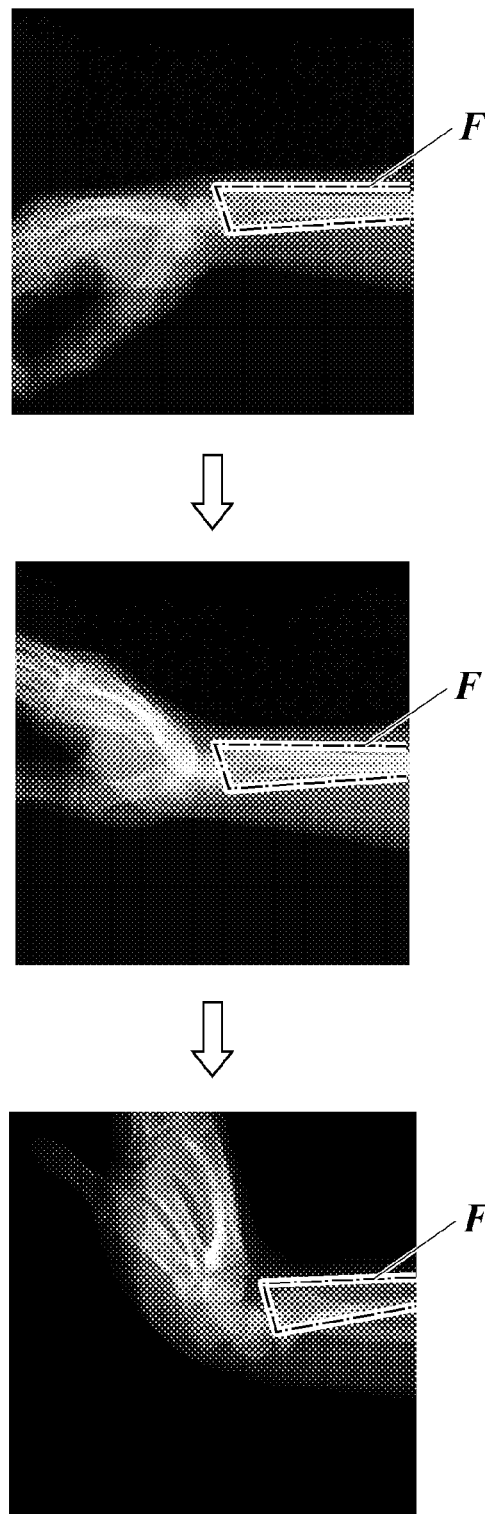
FIG. 9 is a diagram showing how to perform three-dimensional correction of the specific site captured in the radiation moving image.

For example, as shown in FIG. 9, three-dimensional rotation is performed so that the end four points of a bone position of a non-moving portion F, an intersection of diagonal lines of the end four points of the bone position, and a center of gravity of a bone area are constant. Alternatively, three-dimensional rotation is performed so that the number of portions overlapping with the bone of the non-moving portion F becomes the largest.

In the determining process, when it is determined that the radiation R is irradiated to the specific site $B_1$ to be orthogonal to the movable plane P (step S2: Yes), the controller 31 skips the correction process and progresses to the next process.

Here, the controller 31 functions as the determiner by performing the above-described determining process.

After determining Yes in the determining process, or the three-dimensional correction is performed, the controller 31 performs the analysis process (step S5).

As described above, the controller 31 according to the present embodiment performs the analysis based on the radiation moving image obtained by irradiating the radiation R to the specific site $B_1$ so as to be orthogonal to the movable plane P.

In the analysis process, the controller 31 calculates the difference between the signal value of the pixel included in the specific site $B_1$ in one frame included in the radiation moving image and the signal value of another pixel with the same coordinates as the pixel in another frame adjacent to the one frame.

Then, based on the calculated difference, the controller 31 further calculates at least one of the moving distance, the speed, acceleration, and movable range in the specific site $B_1$.

In the analysis process, the controller 31 detects the non-continuous change in the movement of the specific site $B_1$ based on the calculated difference.

Specifically, based on the calculated difference, the controller 31 calculates the speed or the acceleration of the specific site $B_1$ in each frame, and determines for each frame whether an amount of change in the speed (difference between the speed calculated in the previous frame) or the acceleration exceeds a predetermined threshold.

Then, when the change amount of speed or the acceleration exceeds a predetermined threshold in a certain frame, the non-continuous change in the movement occurs in the timing that the frame is generated.

The controller 31 functions as the analysis unit by performing the above-described analysis process.

After the analysis of the dynamic state of the specific site $B_1$ is performed, the controller 31 according to the present embodiment performs the second storage process (step S6), and the dynamic analysis process is finished.

In the second storage process, the controller 31 stores the analysis result of the dynamic state of the specific site $B_1$.

Timing Information Applying Function

The controller 31 according to the present embodiment includes a function to attach to the obtained radiation moving image data the timing information showing the timing that the above external information is detected.

For example, when the radiation detector 2 generates the frame and transmits the frame immediately to the dynamic analysis apparatus 3, the timing information is attached to the frame received when the information detection signal is received.

When the radiation detector 2 and the dynamic analysis apparatus 3 each include a timekeeping function, the information of the time generated for each frame and the time that the information detection signal is received are each attached as the timing information.

According to the above, it is possible to show the timing that the external information is detected while the specific site $B_1$ moves (the degree of bending the joint when the pain occurs) when the moving image is played.

Playing Function

The controller 31 according to the present embodiment includes a function to play the radiation moving image which the radiation detector 2 generated.

When the analysis of the dynamic state of the specific site $B_1$ is finished, the controller 31 according to the present embodiment is able to play the radiation moving image while displaying the analysis result.

The controller 31 changes the way the radiation moving image is played based on the external information detected by the information detector 5.

Specifically, based on the timing information attached to the data of the radiation moving image, the controller 31 decreases the playing speed of the radiation moving image from the frame generated when the information detector 5 detects the external information.

The controller 31 functions as the player which includes such playing function.

According to the above, it is possible to carefully observe the dynamic state of the specific site $B_1$ after the external information is detected.

3. Effect

The system 100 according to the present embodiment as described above analyzes the dynamic state of the specific site $B_1$ based on the radiation moving image continuously imaging the movement of the specific site $B_1$ along the movable plane P from the start of imaging to the end. Therefore, when the change in the movement occurs non-continuously during the movement, the non-continuous change in the movement can be detected.

The system 100 leaves the movement of the specific site $B_1$ as the radiation moving image, and therefore it is possible to review the movement again and again after imaging at any timing.

Therefore, according to the system 100, the diagnosis can be easily performed for the specific site $B_1$ in which non-continuous change occurs in the movement.

When only the radiation image is played, the moment that the movement of the specific site $B_1$ changes non-continuously is displayed at some point.

Therefore, depending on the skill of the person who performs the diagnosis, the playing speed of the radiation moving image, and the degree of the non-continuous change in the movement, it may be relatively easy to perform diagnosis of the specific site $B_1$ by simply looking at the displayed radiation moving image.

In this case, in the analysis process in the dynamic analysis process, instead of calculating the difference of the signal value, typical image processing such as noise removal is performed in each frame.

4. Others

The present invention is described based on the above embodiments, but the present invention is not limited to the above embodiments, and the present invention can be suitably changed without leaving the scope of the present invention.

For example, according to the present embodiment, the specific site as the imaging target is the patella $B_1$, the elbow joint $J_1$, and the shoulder joint $J_2$. However, the system 100 is able to analyze as the specific site a site which normally moves smoothly but which does not move normally when there is an abnormality and the movement is difficult to capture with a still image.

According to the above embodiment, the dynamic analysis apparatus 3 includes a detection information applying function and a playing function, but such functions do not have to be included in the dynamic analysis apparatus 3 and can be included in the console 4.

Figure 10:
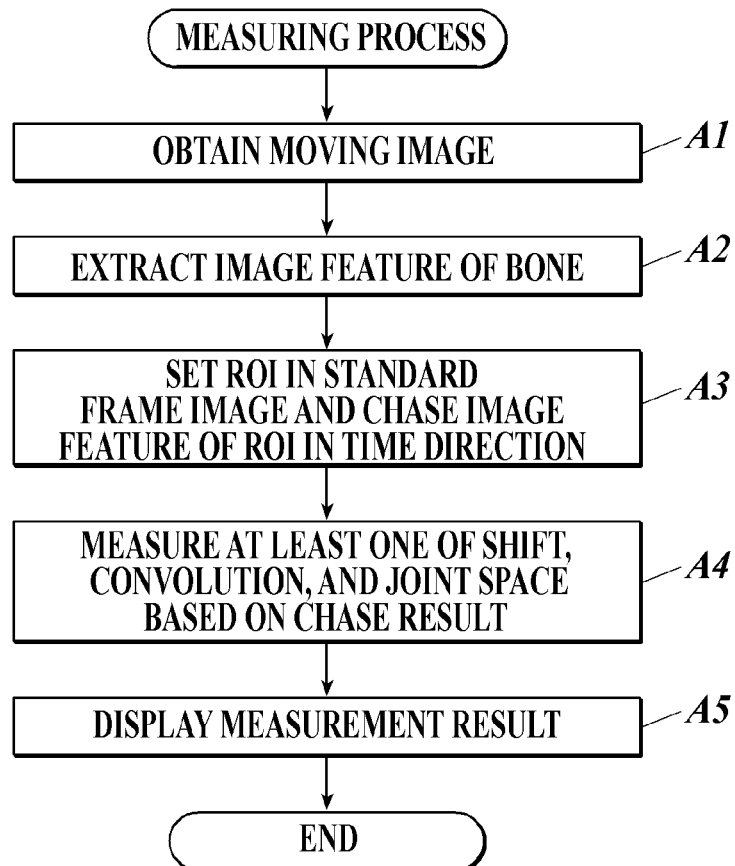
FIG. 10 is a diagram showing a flowchart showing a measurement process performed by the controller shown in FIG. 7.

When the radiation generating apparatus 1 and the radiation detector 2 repeatedly perform radiation imaging a plurality of times on a subject including a plurality of bones aligned connected (for example, joints (including joints and adjacent bones) such as knee joint, hip joint, elbow joint, hand joint, leg joint, intervertebral joint, chin joint, and shoulder joint, and plurality of bones such as carpal bone, tarsal bone, and vertebra) and the radiation moving image including a plurality of frame images is imaged, the controller 31 of the dynamic analysis apparatus 3 executes the measurement process shown in FIG. 10 in coordination with the program stored in the storage 33.

First, the controller 31 obtains the radiation moving image transmitted from the radiation detector 2 (step A1).

That is, in step A1, the controller 31 obtains the radiation moving image of the subject including a plurality of bones aligned connected.

Next, the controller 31 analyzes each frame image in the obtained radiation moving image and extracts an image feature of the bone (step A2).

For example, in step A2, a space filtering process is performed on each frame image to emphasize the outline and the structure of the inside of the bone (for example, bone structure such as cortical bone, cancellous bone, (trabecular bone)), and an edge emphasizing image showing features of the structure of the bone is generated. Alternatively, a texture feature amount such as a co-occurrence matrix is calculated in the bone region and a texture feature image showing a bone texture feature is generated. The image feature to be extracted is determined based on the type of the target of measurement.

Next, the controller 31 sets an ROI (region of interest) in at least one bone in a standard frame image and chases the image features in the set ROI in a time direction (step A3).

Here, the standard frame image is to be a first frame image, for example, but can be any frame image.

As the method to set the ROI, the standard frame image is divided in a unit of blocks including a plurality of pixels, and the block unit in the position (a position in at least one bone) determined in advance according to the imaging site and the type of the measuring target is set as the ROI. In the diagrams and the description which follow, T shows the standard frame image and T+t shows a frame image imaged t seconds after the standard frame image (t is variable).

As another example of the setting method of the ROI, the feature point based on the image feature of the bone extracted in step A2 can be obtained and the surrounding region of the feature point (for example, n pixels×n pixels (n is a positive integer) with the feature point as the center) can be set as the ROI. It is determined in advance which points are to be the feature points based on the imaging site and the type of the measurement target.

Regardless of the setting method, the ROI is to be set in at least one bone of the standard frame image. For example, one or more ROI can be set inside or on the outline of one or more bones, the ROI can be set on one entire bone, or the ROI can be set on the joint including two bones.

Figure 11:
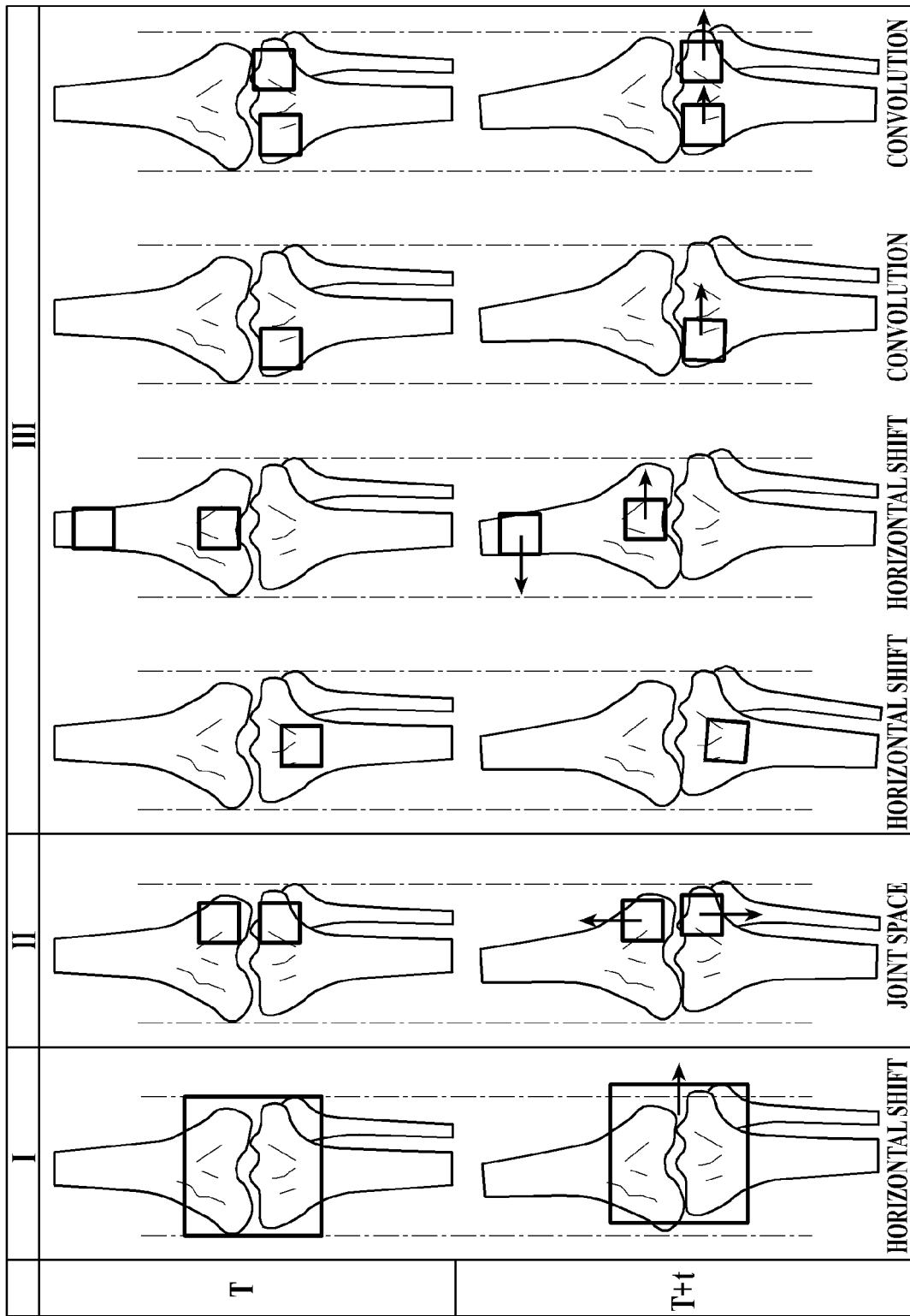
FIG. 11 is a diagram showing another example of a setting method of a region of interest.

The number of ROIs which are set is not limited. For example, as shown in I in FIG. 11, if one ROI is set in a joint including two bones, a horizontal shift (disposition) becomes easy to understand. As shown in II in FIG. 11, if one or more ROIs are set in each bone with a different joint, a joint space becomes easy to understand. As shown in III in FIG. 11, if one or more ROIs are set in the same bone, a convolution (twist) and a horizontal shift (angle change) becomes easy to understand. When the convolution is obtained, the measurement accuracy is more enhanced if there are two or more ROIs.

As a method to chase in the other frame images the image feature in the ROI set in the standard frame image, for example, there is template matching in which the image region of the ROI set in the standard frame image is the template image. That is, the region including the image feature the same as the ROI set in the standard frame image can be chased in another frame image (chased in the time direction). Based on a chase position result in the plurality of frame images, the chase position in the specific frame image can be corrected. For example, when the chase position is greatly shifted, the chase position can be corrected based on the chase position information in the adjacent frame image.

Next, based on the chase result of the ROI, the controller 31 measures the change over time in at least one of the shift in the bone or the joint where the ROI is set, the convolution, and the joint space (step A4).

Below, the measuring method in step A4 is described. Here, measurement of the change over time in the following is described, horizontal shift in the joint (joint bone), convolution, joint space, the shift in the vertebra, and the convolution. Here, the knee joint is described as the example of the joint and the lumbar is described as the example of the vertebra. Alternatively, the other joints and the vertebra can be measured by similar methods.

(Measurement of Horizontal Shift in Joint (Bone))

Due to ligament injury and decrease in cartilage, horizontal shift of the joint position (bone around joint) may occur. For example, in the knee joint, a horizontal shift occurs in the horizontal direction when a burden is applied and this is called a thrust.

As the index to quantitatively evaluate the horizontal shift of the joint, according to the present embodiment, the change over time in a displacement amount Si (valgus amount or varus amount, see FIG. 12) and/or an angle change θ is measured.

Figure 12:
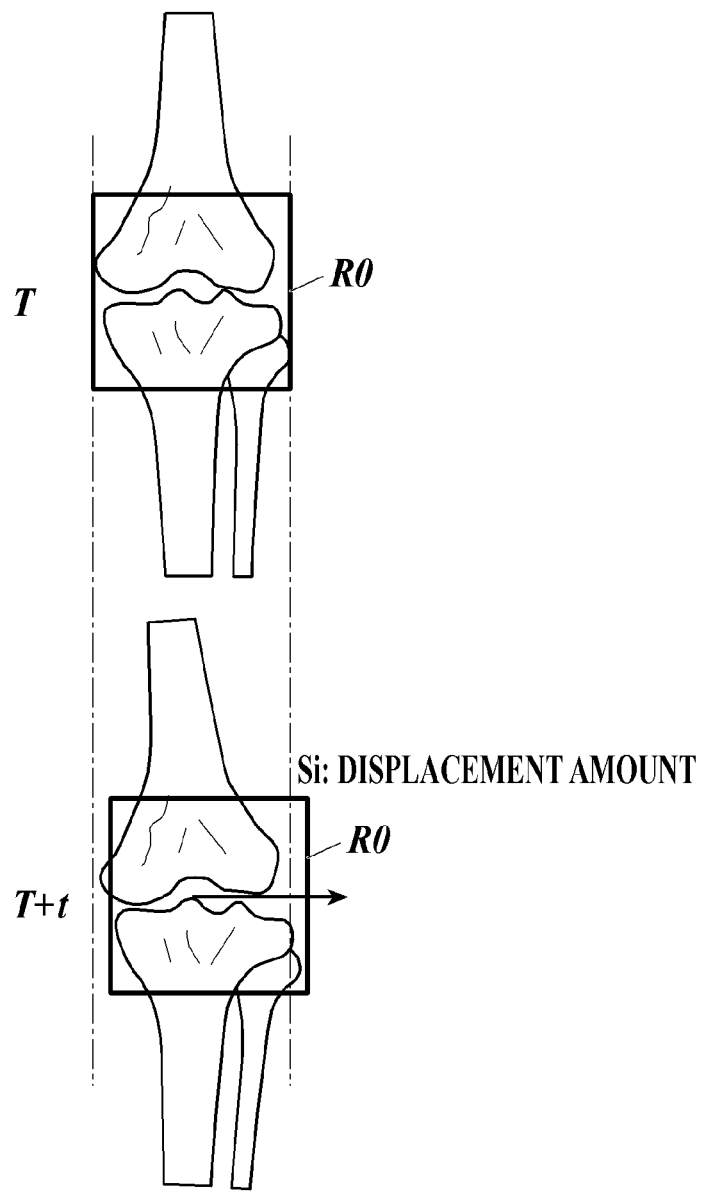
FIG. 12 is a diagram showing a method to measure a displacement amount Si in a horizontal shift of a knee joint.

As shown in FIG. 12, the displacement amount Si is the displacement amount in the left and right direction (horizontal direction) between the ROI (R0) set in the knee joint in the standard frame image T, and the R0 chased in the frame images T+t. The position (coordinates) itself of the ROI can be considered to be the displacement amount.

Although the above is described as the displacement amount in the horizontal shift of the joint, that is, the displacement amount of the joint in the left and right direction is the displacement amount Si, the direction is not limited to the left and right direction, and the shift (displacement amount) can be measured considering the displacement amount in the horizontal direction of the joint (that is, the vertical direction and the diagonal direction).

The angle change θ is the change in the angle in each frame image from the standard frame image of the bone in the joint. In order to measure the angle change θ, the change in the angle of the bone in the joint is measured to measure the horizontal shift of the bone and the joint including the bone.

The angle change θ can be measured using chase results of two or more ROIs, or can be measured using the chase result of one ROI.

When the measurement is performed using the chase result of two or more ROIs, for example, the angle formed by the line 11 connecting the center points of the two ROIs (R1 and R2) set vertically on an axis of a thigh bone or shin bone in the standard frame image T and the line 12 connecting the center points of R1 and R2 chased in each frame image T+t is measured as the angle change θ.

When the measurement is performed using the chase result of one ROI, for example, the angle (tilt of ROI) formed by one side of the ROI (R3) set on the axis of the thigh bone or the shin bone in the standard frame image T and one side corresponding to the R3 chased in each frame image T+t is measured as the angle change θ.

Conventionally, there is no method to dynamically and quantitatively evaluate the horizontal shift of the joint (bone), and the evaluation relied on subjective evaluation of the doctor. Turning to the present invention, by measuring the change over time in the displacement amount Si or the angle change θ, the change in the degree of the horizontal shift (valgus or varus) in the joint (bone) over time can be understood quantitatively. The degree of ligament injury, whether dislocation or fracture exists, and degree of severity of osteoarthritis can be easily understood. With this, the accuracy of diagnosis is enhanced and the variation in diagnosis among doctors and facilities can be decreased.

The angle change θ can be used as an alternative of FTA. In order to calculate conventional FTA, the entire leg needed to be imaged and the amount of irradiation on the patient is large. According to the present method, the calculation is possible with the image around the joint. Therefore, the amount of irradiation can be reduced.

(Measurement of Joint Space) The joint space (interval between bones in the joint) becomes smaller as the ligament injury, osteoarthritis, and the cartilage wearing becomes more severe.

As an index to quantitatively evaluate the joint space, according to the present embodiment, the change over time in a length D (refer to FIG. 13) in the joint space is measured.

Figure 13:
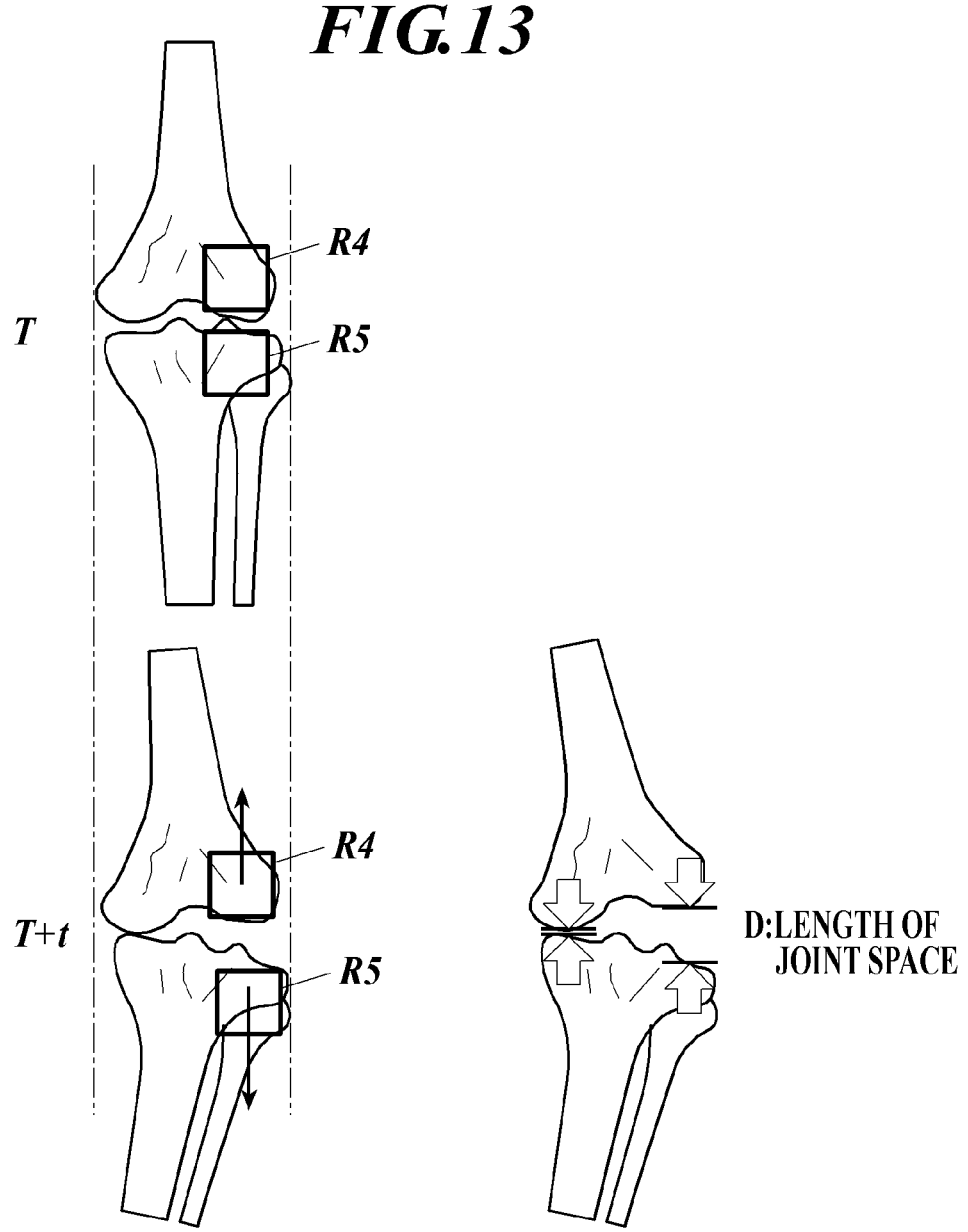
FIG. 13 is a diagram showing a method to measure a length D of a joint space of a knee joint.

As shown in FIG. 13, the length D in the joint space is a distance between two ROIs (R4, R5) set in the outline of two adjacent bones in the joint.

As change over time in the length D of the joint space is measured, the change of the degree of joint space over time can be quantitatively understood, and the degree of ligament injury, severity of osteoarthritis, degree of wearing of the cartilage, whether dislocation or fracture exists and whether the bone is able to move can be easily understood. Although it is useful to measure the length D of the joint space alone, by combining with the displacement amount Si and the angle change θ, it is possible to understand the state of the joint and the ligament in more detail.

(Measurement of Convolution of Bone)

When the ligament around the joint and the cartilage is damaged, the bone of the joint slips in the front and back direction and convolution (external rotation or internal rotation) occurs. That is, the degree and the direction of convolution of the bone in the joint is understood. With this, the degree of damage in the ligament around the joint and the degree of damage in the cartilage (degree of being caught) can be understood.

As the index to quantitatively evaluate the convolution, according to the present embodiment, the change in a convolution amount Ar and/or a convolution angle φ over time is measured.

Figure 14:
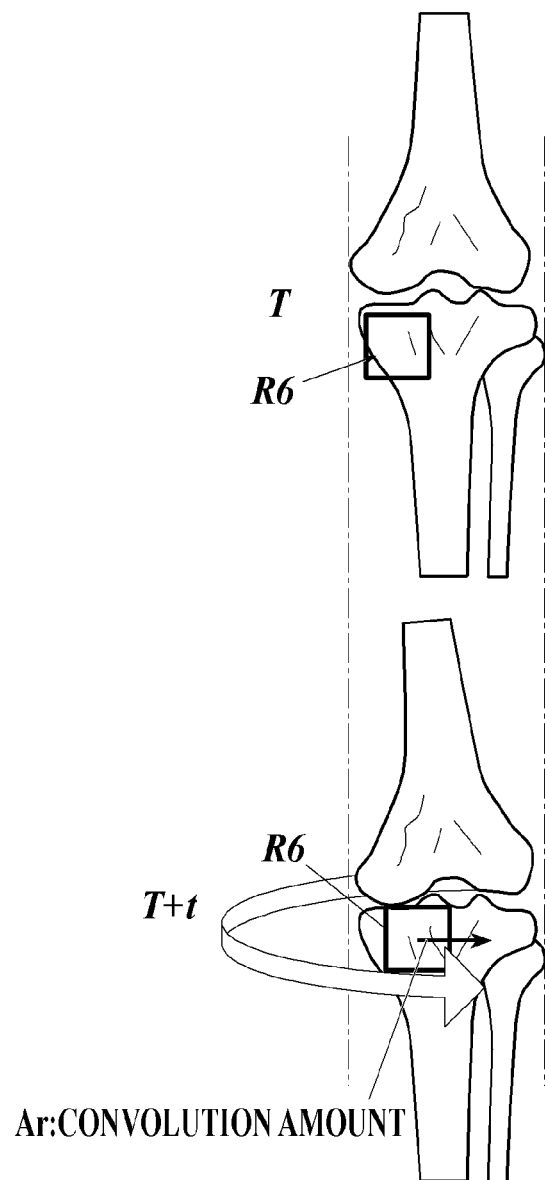
FIG. 14 is a diagram showing a method to measure a convolution amount Ar of a knee joint.

For example, as shown in FIG. 14, the convolution amount Ar is the displacement amount of the ROI (R6) set in the portion including the image feature showing the trabecula of the bone in the joint in the standard frame image T (here, thigh bone or shin bone) in the left and right direction (horizontal direction) of the R6 chased in each frame image.

By measuring the change over time in the convolution amount Ar, the change over time in the degree and the direction of the convolution of the bone in the joint can be understood. The convolution amount Ar is related to the twist in the joint (slide in the front and back direction). Therefore, it becomes easier to understand the degree of damage in the ligament around the joint and the degree of damage in the cartilage (degree of being caught).

(Measurement in Shift of Vertebra)

There may be a shift in the vertebra when spondylolysis or spondylolisthesis occurs.

In the radiation moving image imaging the lumbar and the cervical spine as the subject, the change in the shift of the vertebra over time is measured. The example described here shows the measuring of the change in the shift of the vertebra L3 over time.

As an index to quantitatively evaluate the shift of the vertebra, according to the present embodiment, the change in the displacement amount of the vertebra (distance D2 between vertebrae, distance D3 between the vertebra and sacrum, relative displacement amount Sit between vertebra and sacrum, and/or relative angle change amount θd) over time is measured.

Figure 15A:
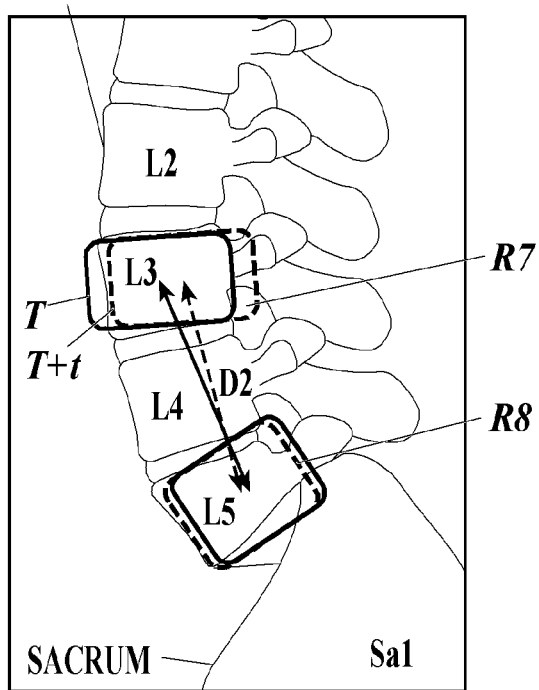
FIG. 15A is a diagram showing a method to measure a distance D2 between vertebrae.

As shown in FIG. 15A, the distance D2 between the vertebrae is the distance between ROI (R7) set (chased) in the vertebra L3 in each frame image and the ROI (R8) set (chased) in the vertebra L5 in each frame image (for example, distance set between the centers of the two ROI). The distance is not limited to the vertebra L3 and L5, and the distance between other vertebrae can be obtained.

Figure 15B:
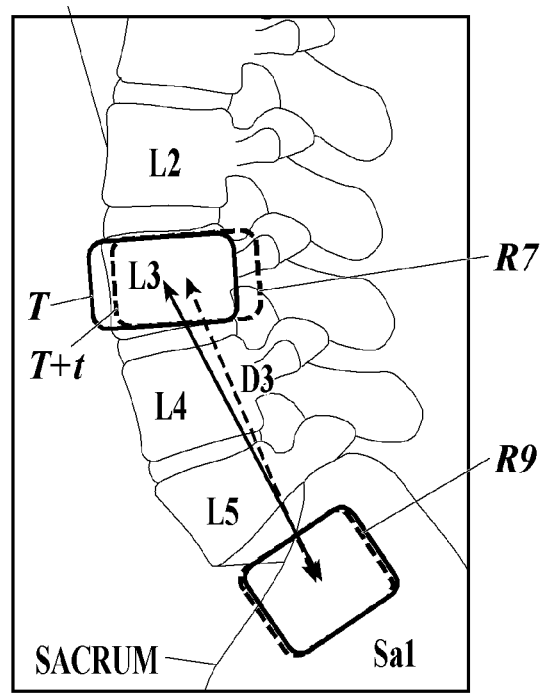
FIG. 15B is a diagram showing a method to measure a distance D3 between a vertebra and a sacrum.

As shown in FIG. 15B, the distance D3 between the vertebra and the sacrum is the distance between the ROI (R7) set (chased) in the vertebra L3 in each frame image and the ROI (R9) set (chased) in the sacrum Sa1 in each frame image (for example, distance between centers of the two ROI).

Figure 16A:
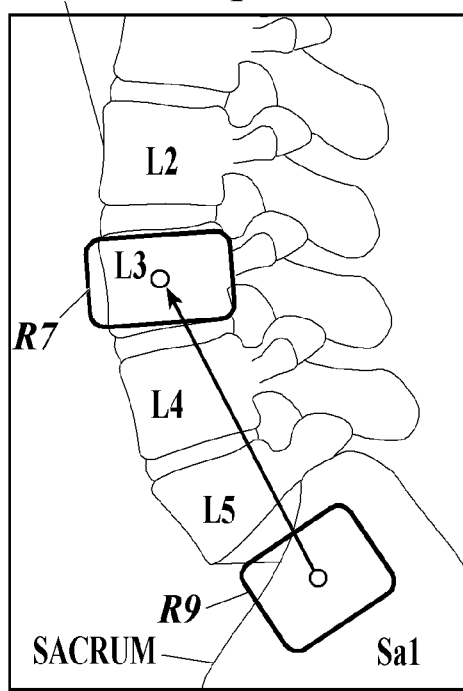
FIG. 16A is a diagram showing a method to measure a relative displacement amount Sit between the vertebra and the sacrum.
Figure 16B:
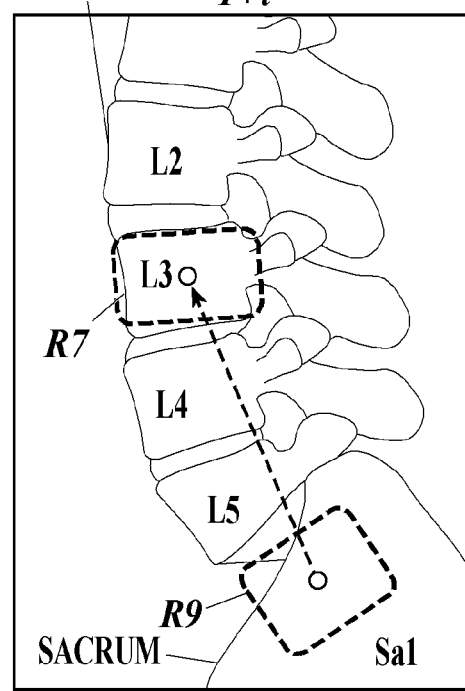
FIG. 16B is a diagram showing a method to measure a relative displacement amount Sit between the vertebra and the sacrum.
Figure 16C:
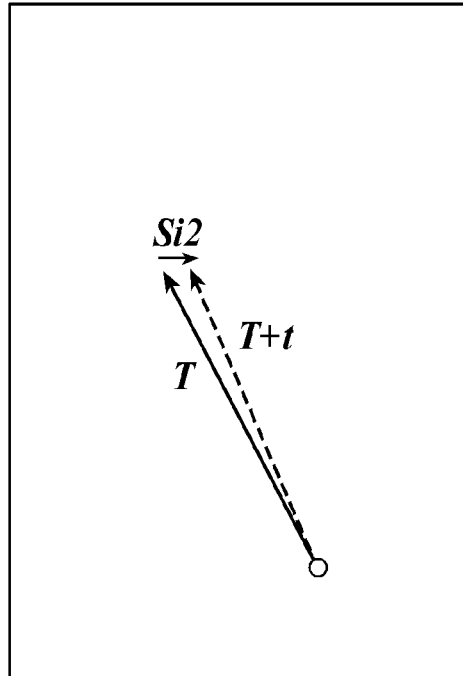
FIG. 16C is a diagram showing a method to measure a relative displacement amount Sit between the vertebra and the sacrum.

The relative displacement amount Sit between the vertebra and the sacrum is the displacement amount when the ROI (R7) set in the vertebra L3 in the standard frame image T shown in FIG. 16A and the ROI (R9) set in the sacrum Sa1 in R7 set (chased) in the vertebra L3 in each frame image T+t are the standards (see FIG. 16C). The bone is not limited to the vertebra L3, and the relative displacement amount Sit between other vertebra and the sacrum can be obtained.

By measuring the change in the distances D2, D3 or the relative displacement amount Sit over time, it is possible to understand whether there is spondylolysis and spondylolisthesis in the vertebra, and it is easier to understand the severity. Conventionally, there is no clear standard to determine the treatment plan (especially type of operation) for the spondylolysis and spondylolisthesis in the vertebra, and there is a tendency to rely on the subjectivity of the doctor in charge. Therefore, there is a problem that there is a variation in the quality of medicine among the hospitals and the doctors. By selecting the treatment plan (type of operation) based on the quantitative amount value obtained from the above measurement method, the doctor is able to provide to the patient medical care which is high in accuracy and high in reproducibility.

Preferably, the relative displacement amount Sit makes it easier to understand the moving direction of the target vertebra L3, and this point cannot be understood by distances D2 and D3. From the viewpoint of calculating the shift amount (slide amount) of the vertebra, it is preferable to obtain the relative displacement amount Sit for the adjacent vertebra.

(Calculation of Changing Speed and Acceleration)

The change over time in the changing speed and the acceleration of the above-described measurement values (displacement amount Si, convolution amount Ar, etc.) can be measured as an index showing the shift of the bone and the joint, the convolution, and the joint space.

By using the measured speed and the acceleration, a shock value G shown in (formula 1) and shock force Fi shown in (formula 2) can be calculated. With this, it is possible to estimate the burden and load on the body quantitatively.

Shock Value $G$=speed right before stopping÷amount of time until stopping  (formula 1)

Shock Force $Fi$=mass×acceleration  (formula 2)

When the measurement in step A4 ends, the controller 31 displays the measurement result on the display 34 (step A5) and ends the measurement process.

In step A5, for example, only the measurement result can be displayed on the display 34, and the measurement result measured from each frame image can be displayed corresponded with the frame image (for example, overlapped). Here, each frame image can be displayed switched on one screen (moving image display), the frame image can be aligned in order on one screen and displayed, or the frame image can be displayed on a different screen for each frame image.

When the radiation moving image (frame image) is displayed together with the measurement result, the imaged image can be displayed or the feature amount image such as the edge emphasized image and the texture feature image generated in step A2 can be displayed.

Figure 17:
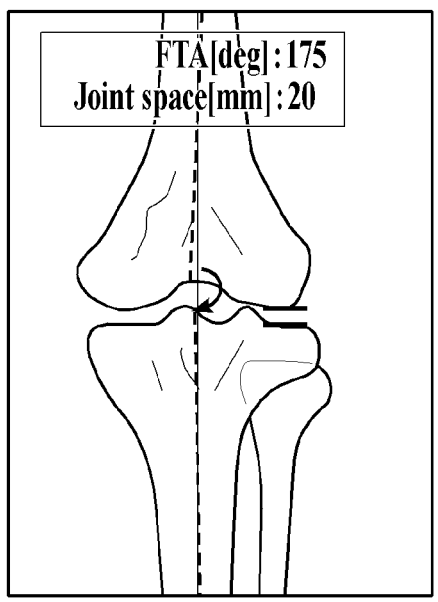
FIG. 17 is a diagram showing an example of a display of a measurement result.

FIG. 17 is a diagram showing an example of a display when the measurement result is shown with numeric values displayed overlapped on the frame image as the source of measurement. As shown in FIG. 17, by displaying the measurement result corresponded with the frame image as the source of measurement, the user is able to easily understand the measurement result in each frame image.

The change amount (speed) of the measurement value for each unit of time and the changed direction are displayed as a vector or the change amount (speed) of the measurement value for each unit of time and the changed direction are shown with a corresponding pixel color. With this, the state of the change in the bone and the joint due to the shift, convolution, and joint space can be understood two dimensionally. Therefore, the movement of the bone and the joint can be understood with more detail. Further, the acceleration of the change in the measurement value and the acceleration direction can be displayed with a vector or color.

By overlapping the vector or color on the radiation moving image and displaying the radiation moving image, the state of change in the horizontal shift (valgus/*varus*), convolution (internal rotation/external rotation), and the change in the joint space can be intuitively understood on the image. Since it is possible to watch the radiation moving image while predicting the next direction of movement, the burden of interpreting the image decreases. Moreover, it becomes easier to understand the medical state (which ligament is bad).

Further, for example, the measurement result can be displayed as a graph.

Figure 18A:
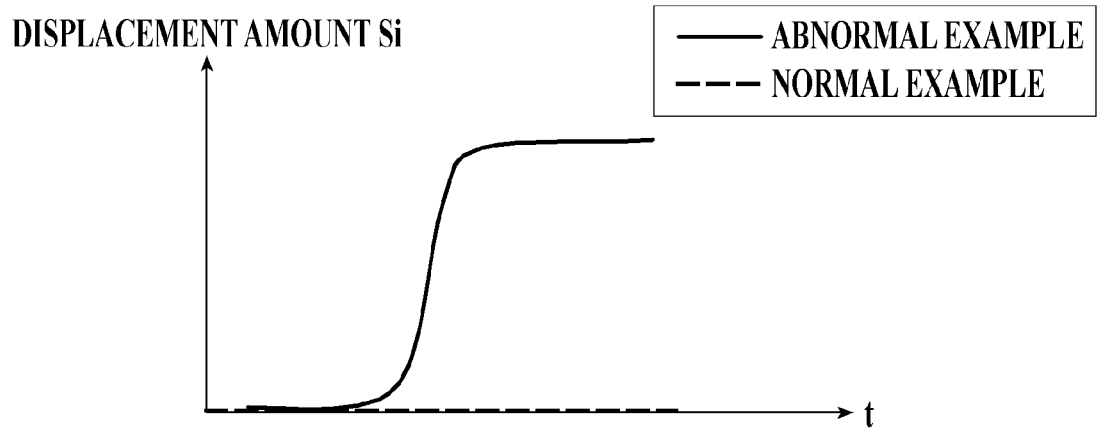
FIG. 18A is a diagram showing an example of a graph display of a measurement result.

FIG. 18A is a diagram showing a graph showing a measurement result (displacement amount S) of a normal example and an abnormal example of a horizontal shift in the knee joint when the imaging is performed at a timing when weight is placed on one foot or both feet intentionally in a standing position (taking a step), or when staying still on one foot or both feet in a standing position. As shown in FIG. 18A, horizontal shift hardly occurs in the normal example. Therefore, the graph is a straight line substantially horizontal. In the abnormal example, (for example, the cartilage or ligament is damaged), horizontal shift occurs. Therefore, the graph shows the value increasing at the timing when the horizontal shift occurs. According to such display of the graph, it becomes easy to understand at which timing the horizontal shift starts, and it becomes easier to understand the medical state, and the severity of the symptoms such as osteoarthritis of the knee.

Figure 18B:
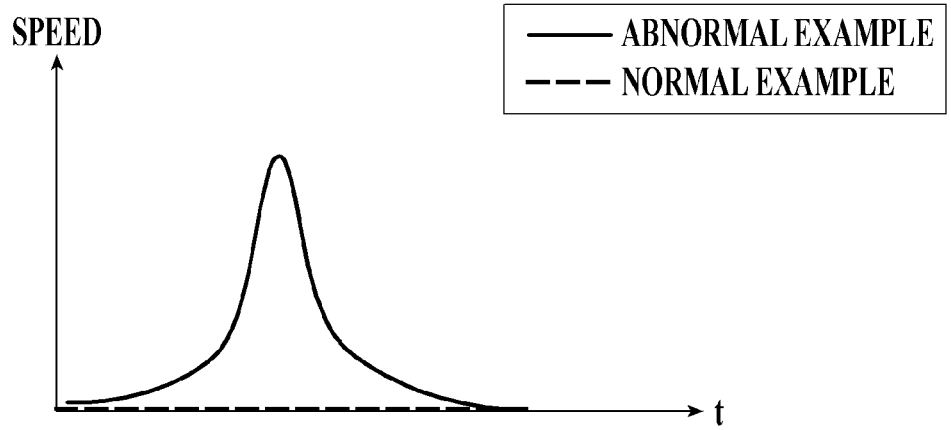
FIG. 18B is a diagram showing an example of a graph display of a measurement result.

FIG. 18B is a graph showing the speed of the normal example and the abnormal example shown in FIG. 18A (change speed in measurement value). As shown in FIG. 18B, by displaying the speed as the graph, even if the horizontal shift is small, the change can be emphasized, and the timing that the horizontal shift occurs can be easily understood.

Figure 19A:
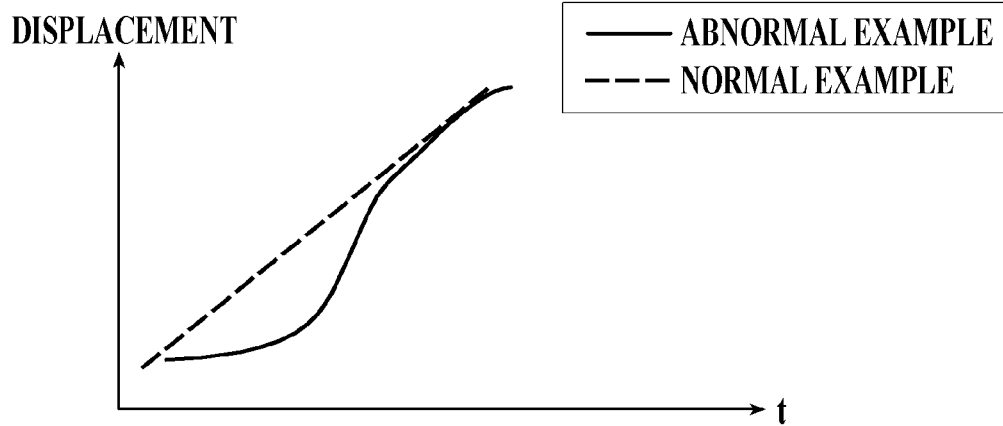
FIG. 19A is a diagram showing an example of a graph display of a measurement result.

FIG. 19A is a diagram showing a graph of the measurement result of the displacement in the normal example and the abnormal example, when the region of interest (for example, elbow joint) is moved at a certain speed using a jig. As shown in FIG. 19A, in the normal example, the position changes at the speed specified by the jig, but in the abnormal example (being caught), the position changes at a timing different from the speed specified in the jig. According to such graph display, normal/abnormal can be easily determined.

Figure 19B:
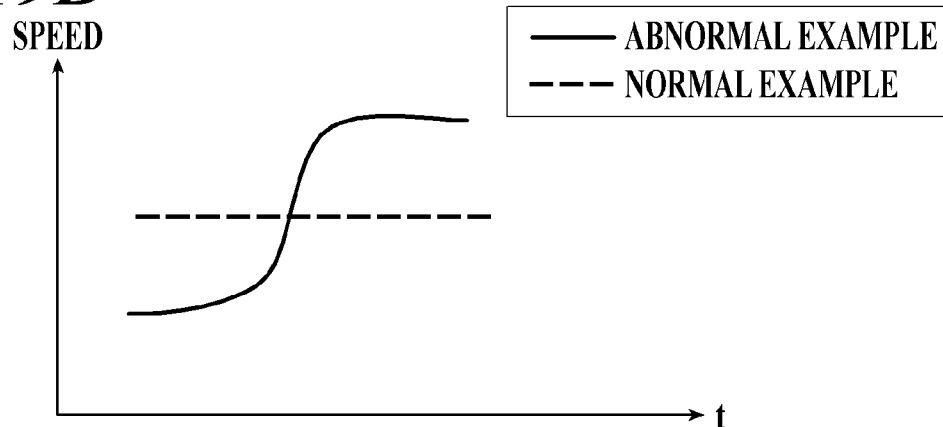
FIG. 19B is a diagram showing an example of a graph display of a measurement result.

FIG. 19B is a diagram showing a graph of the speed (changing speed of the measurement value) in the normal example and the abnormal example shown in FIG. 19A. As shown in FIG. 19B, by displaying the speed as a graph, even if the displacement amount in the region of interest is small, it is easy to determine normal and abnormal. Moreover, it is easy to determine at which timing there is catching or there is sudden movement.

Figure 19C:
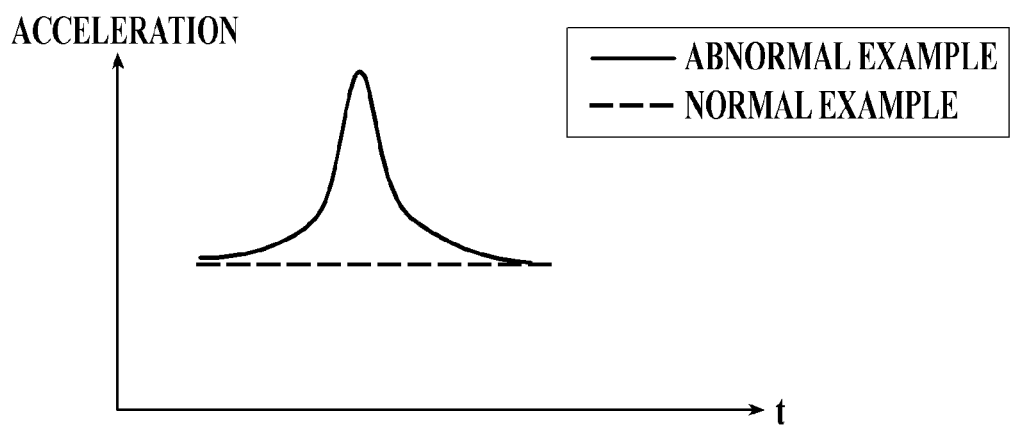
FIG. 19C is a diagram showing an example of a graph display of a measurement result.

FIG. 19C is a diagram showing a graph of the acceleration (acceleration of the change of the measurement value) in the normal example and the abnormal example shown in FIG. 19A. As shown in FIG. 19C, by displaying the acceleration as a graph, even if the actual change in speed in the region of interest is small, it becomes easy to determine normal and abnormal. Further, it is easy to understand the timing when the acceleration is increased and the acceleration is decreased. Therefore, it is easy to understand the timing when there is a burden on the body.

The frame image in which the measurement result satisfies a predetermined condition can be displayed on the display 34 as the initial display frame of the radiation moving image. Alternatively, similarly, only the span of the frame images in which the measurement result satisfies a predetermined condition may be played.

Figure 20A:
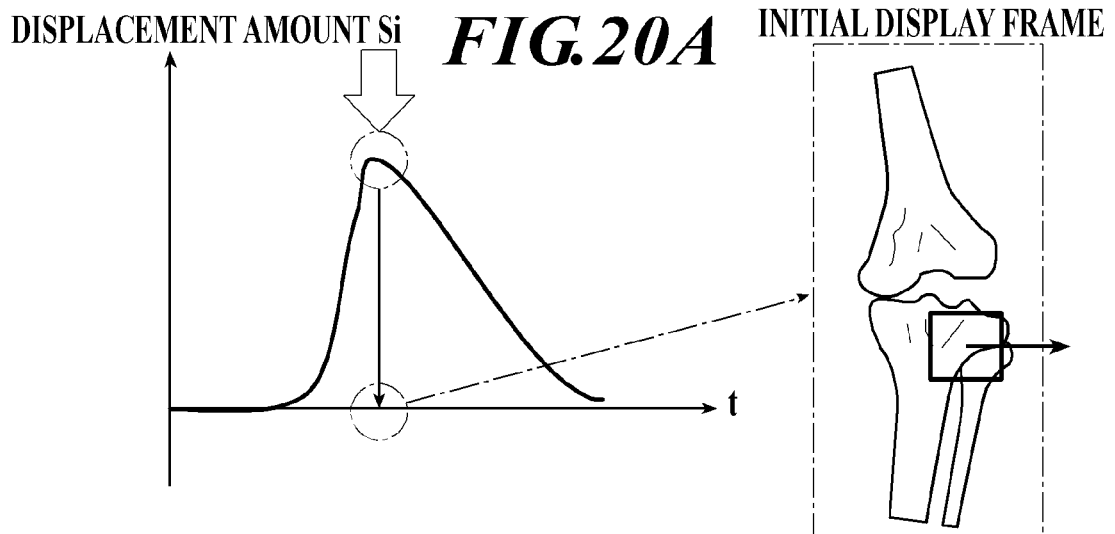
FIG. 20A is a diagram describing a selection method of a frame image to be initially displayed.

FIG. 20A shows a case in which the frame with the largest displacement amount is initially displayed.

Figure 20B:
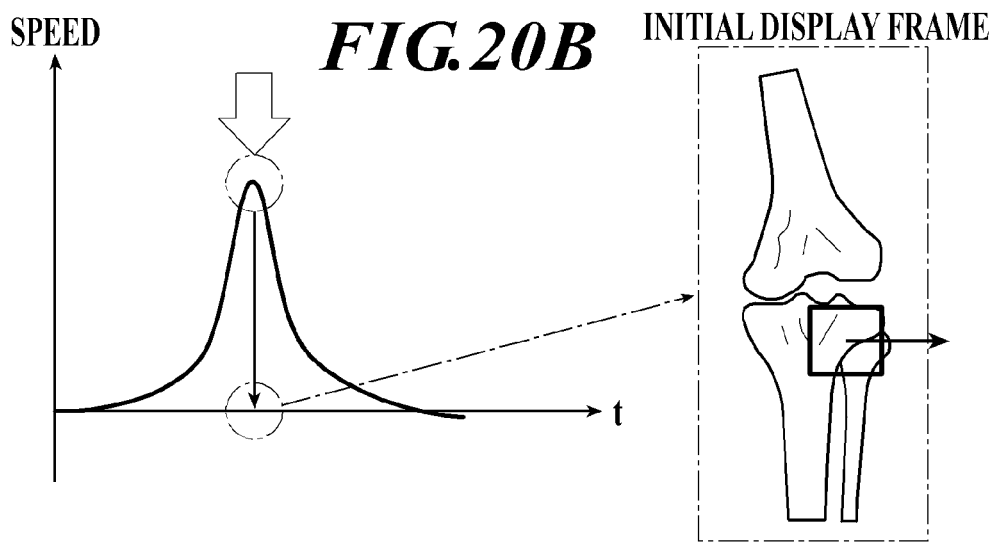
FIG. 20B is a diagram describing a selection method of a frame image to be initially displayed.

FIG. 20B shows a case in which the frame with the largest speed is initially displayed.

Figure 20C:
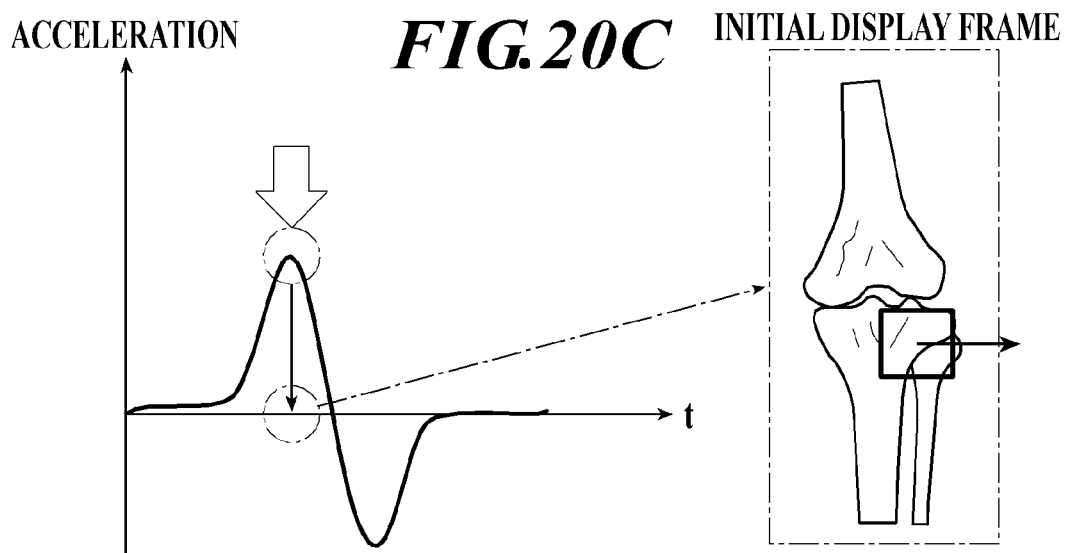
FIG. 20C is a diagram describing a selection method of a frame image to be initially displayed.

FIG. 20C shows a case in which the frame with the largest acceleration is initially displayed.

Viewing all of the radiation moving images is a large burden to the user, however, by initially displaying the important frame images which satisfy predetermined conditions, the user is able to interpret with priority the clinically important frame images. Consequently, the diagnostic work flow is enhanced.

When the cartilage is worn or the ligament is damaged (peel, contracture), there are cases such as moving in a direction to which the part does not move in a healthy state, or not being able to move in the direction to which the part is supposed to move. By quantitatively showing the movement of the bone and the joint according to the above measurement process, it becomes easy to understand the severity and to analyze the reason of the main symptom such as pain (classifying from fractures, ligament damage, muscle damage, meniscus damage, dislocation, pseudo joint, etc.). Further, objectivity increases, and the variation in diagnosis among those who perform the diagnosis decreases. That is, the reproducibility of diagnosis is enhanced.

The measurement result measured in the measurement process is stored in the database 41 corresponded to the corresponding frame image in the radiation moving image.

As described above, according to the measurement process, the movement in the timewise direction for the displacement direction, displacement timing, speed, and acceleration of the affected part due to the shift in the bone and joint, convolution, and joint space can be quantitatively shown. Therefore, the accuracy of diagnosis and the reproducibility of the diagnosis for the bone and the joint can be enhanced. Further, there is no need to perform the moving image imaging in a large range such as imaging the entire leg to measure FTA as in the conventional technique. Therefore, the amount of irradiation can be suppressed.

According to the present embodiment, calculating the displacement amount, the change in the angle, the convolution amount, and the convolution angle from the standard frame image are described. However, the displacement amount, the change in the angle, the convolution amount, and the convolution angle from the adjacent frame image can be calculated. According to the above, the movement of the bone and joint can be understood more intuitively.

Modification 2

The controller 31 may calculate an instability index F showing instability of the movement based on the measurement result in step A4. The instability index F is an index showing how much time the bone or the joint is displaced non-continuously. According to the instability index F, the qualitative instability is shown quantitatively. Therefore, the reproducibility of the diagnosis increases, and comparison over time becomes easier.

The following is used as the instability index F, for example, dispersity, standard deviation, or change coefficient (standard deviation÷ average value) within a certain amount of time for the displacement amount Si, angle change θ, convolution amount Ar, convolution angle φ, relative displacement amount Sit, relative angle change amount θd, convolution amount Art, distances D2 and D3, or the speed or the acceleration of the above. For example, there are standard deviation of Si, dispersion of the speed of θ, and change coefficient of acceleration of φ. Such instability index F displays a numeric value or a graph on the display 34, and with this, the instability of the movement can be easily understood.

The controller 31 of the dynamic analysis apparatus 3 executes the above-described measurement process in coordination with the program stored in the storage 33 to function as the following units in the image processing apparatus.

An image processing apparatus includes an image obtaining unit which obtains the radiation moving image of the subject including a plurality of bones aligned connected, an extracting unit which extracts an image feature of the bone from each of the plurality of frame images included in the radiation moving image, a chasing unit which sets a region of interest on at least one bone in a frame image which is to be a standard among the plurality of frame images and which chases the image feature in the region of interest in a time direction, and a measuring unit which measures the change over time in at least one of a shift, convolution or joint space in a bone in which the region of interest is set or a joint including a bone in which the region of interest is set based on the chasing result by the chasing unit.

Preferably, the measuring unit measures at least one of the displacement amount due to the shift of the bone or the joint, the displacement amount due to the convolution, the length of the joint space, changing speed of the above or the acceleration of the change of the above based on the chasing result by the chasing unit.

Preferably, the image processing apparatus includes a display which displays a measurement result by the measuring unit.

Preferably, the display unit displays the measurement result overlapped on the radiation moving image.

Preferably, moreover, the display unit displays the graph of the measurement result.

Preferably, further, the image processing apparatus includes a calculating unit which calculates an index showing the instability of the movement of the bone or the joint based on the measurement result by the measuring unit.

Preferably, the display unit displays the calculating result by the calculating unit.

Preferably, the image processing apparatus includes the judging unit which judges whether there is instability in the joint based on the measurement result by the measuring unit.

Preferably, the display unit displays the determining result by the determining unit.

Preferably, the storage 33 stores the program to control the computer to perform the following functions, the image obtaining unit which obtains the radiation moving image of the subject including the plurality of bones aligned connected, the extracting unit which extracts the image feature of the bone from each of the plurality of frame images included in the radiation moving image, the chasing unit which sets a region of interest on at least one bone in the frame image which is to be the standard among the plurality of frame images and which chases the image feature of the region of interest in the time direction, and the measuring unit which measures the change over time in at least one of the shift, convolution or the joint space in the bone in which the region of interest is set or the joint including the bone in which the region of interest is set, based on the chase result by the chasing unit.

According to the above description, a hard disk or a semiconductor nonvolatile memory is used as the computer readable medium for the program of the present invention, but the medium is not limited to the above. An example of another computer readable storage medium includes a portable storage medium such as a CD-ROM. Alternatively, a carrier wave can be applied as the medium to provide the data of the program according to the present invention through communication lines.

Although embodiments of the present invention have been described and illustrated in detail, the disclosed embodiments are made for purposes of illustration and example only and not limitation. The scope of the present invention should be interpreted by terms of the appended claims

What is claimed is:

1. A non-transitory computer-readable storage medium storing a program causing a computer to perform an analysis process based on a radiation moving image in which a dynamic state of a specific site of a subject is captured, the program comprising:
the analysis process in which, an analysis is performed based on the radiation moving image wherein when a plane in which the specific site is movable is to be a movable plane, the radiation moving image is obtained by irradiating radiation on the specific site in a state in which the radiation is orthogonal to the movable plane.

2. The storage medium storing a program according to claim 1, wherein, the program further includes a determining process in which, before the analysis process is performed, a determination is made whether the radiation is irradiated on the specific site to be orthogonal to the movable plane when the specific site is imaged.

3. The storage medium storing a program according to claim 2, wherein, in the determining process, the determination of whether the radiation is irradiated orthogonal to the movable plane is made based on a setting state of a radiation irradiator irradiating the radiation on the specific site.

4. The storage medium storing a program according to claim 2, wherein the program further includes a correction process in which, when the determination is made in the determination process that the radiation is not irradiated to the specific site to be orthogonal to the movable plane, three dimensional correction is performed so that it is as if the radiation irradiated to the specific site captured in the radiation moving image is orthogonal to the movable plane.

5. The storage medium storing a program according to claim 1, wherein in the analysis process, a difference between a signal value of a pixel in one frame included in the radiation moving image and a signal value of another pixel with the same coordinates as the pixel in another frame adjacent to the one frame is calculated.

6. The storage medium storing a program according to claim 5, wherein in the analysis process, at least one of a moving distance, speed, acceleration and movable range in the specific site is further calculated based on the calculated difference.

7. The storage medium storing a program according to claim 5, wherein in the analysis process, a non-continuous change in a movement of the specific site is detected based on the calculated difference.

8. The storage medium storing a program according to claim 1, wherein the specific site is a joint or a spine.

9. A dynamic analysis apparatus comprising:
a hardware processor which is configured to perform an analysis based on a radiation moving image in which a dynamic state of a specific site of a subject is captured,
wherein, when a plane in which the specific site is movable is to be a movable plane in the radiation moving image, the hardware processor performs the analysis based on the radiation moving image obtained by irradiating radiation to the specific site to be orthogonal to the movable plane.

10. A dynamic analysis system comprising:
a moving image generator which generates a radiation moving image in which a dynamic state of a specific site of a subject is captured; and
a hardware processor which is configured to perform an analysis based on the radiation moving image,
wherein, when a plane in which the specific site is movable is to be a movable plane in the radiation moving image, the hardware processor performs the analysis based on the radiation moving image obtained by irradiating radiation to the specific site to be orthogonal to the movable plane.

11. The dynamic analysis system according to claim 10, further comprising a storage which stores at least one of a plurality of frames included in the radiation moving image generated by the moving image generator.

12. The dynamic analysis system according to claim 10, further comprising a detector which detects external information occurring while the moving image generator generates the radiation moving image,
wherein, the hardware processor plays the radiation moving image generated by the moving image generator, and
the hardware processor changes how the radiation moving image is played based on the external information detected by the detector.

13. The dynamic analysis system according to claim 12, wherein the hardware processor lowers a playing speed of the radiation moving image from the frame generated when the detector detects the external information.

* * * * *